US011208540B2

(12) United States Patent
Bossolo et al.

(10) Patent No.: US 11,208,540 B2
(45) Date of Patent: Dec. 28, 2021

(54) METHOD OF MAKING CURED PARTS

(71) Applicant: SOLVAY SPECIALTY POLYMERS ITALY S.P.A., Bollate (IT)

(72) Inventors: Stefano Bossolo, Parabiago (IT); Matteo Fantoni, Vanzaghello (IT); Marco Avataneo, Milan (IT); Michael J. Cox, Mesa, AZ (US)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 144 days.

(21) Appl. No.: 16/499,866

(22) PCT Filed: Mar. 23, 2018

(86) PCT No.: PCT/EP2018/057476
§ 371 (c)(1),
(2) Date: Sep. 30, 2019

(87) PCT Pub. No.: WO2018/177940
PCT Pub. Date: Oct. 4, 2018

(65) Prior Publication Data
US 2020/0109257 A1    Apr. 9, 2020

(30) Foreign Application Priority Data

Mar. 31, 2017 (EP) ..................................... 17164042
May 12, 2017 (EP) ..................................... 17170781

(51) Int. Cl.
*C08K 5/03* (2006.01)
*G01M 13/00* (2019.01)
*C08J 3/24* (2006.01)
*G01N 33/44* (2006.01)
*H01L 21/56* (2006.01)
*H01L 23/29* (2006.01)

(52) U.S. Cl.
CPC .................. *C08K 5/03* (2013.01); *C08J 3/24* (2013.01); *G01M 13/00* (2013.01); *G01N 33/445* (2013.01); *C08J 2329/10* (2013.01); *H01L 21/565* (2013.01); *H01L 23/293* (2013.01)

(58) Field of Classification Search
CPC .................................. C08K 5/03; G01M 13/00
See application file for complete search history.

(56) References Cited

U.S. PATENT DOCUMENTS

| 4,281,092 | A | 7/1981 | Breazeale |
| 4,906,917 | A | 3/1990 | Olness et al. |
| 4,920,170 | A | 4/1990 | Abe et al. |
| 4,943,622 | A * | 7/1990 | Naraki ................. C08F 214/18 526/206 |
| 5,447,993 | A | 9/1995 | Logothetis |
| 5,789,489 | A | 8/1998 | Coughlin et al. |
| 5,947,053 | A | 9/1999 | Burnham et al. |
| 6,465,576 | B1 * | 10/2002 | Grootaert ............ C08F 214/262 525/199 |
| 8,075,992 | B2 * | 12/2011 | Iwamoto ................. C08J 7/043 428/336 |
| 2004/0014900 | A1 | 1/2004 | Coggio et al. |
| 2020/0109273 | A1 * | 4/2020 | Bossolo ............... C08K 5/0025 |

FOREIGN PATENT DOCUMENTS

| DE | 3823278 A1 | 1/1989 |
| WO | 9502634 A1 | 1/1995 |
| WO | 2004/009660 A1 | 1/2004 |

OTHER PUBLICATIONS

Reich U., Smart Seals—Seal, Feel, Act, Press release, Apr. 25, 2016, (https://www.fst.com/press/2016/freudenberg-smart-seals).
Office Action issued in corresponding Chinese Application No. 201880022989.2; dated Aug. 30, 2021 (9 pages).

* cited by examiner

*Primary Examiner* — Vickey Nerangis
(74) *Attorney, Agent, or Firm* — Osha Bergman Watanabe & Burton LLP

(57) ABSTRACT

The invention pertains to a method of making cured parts from a composition comprising certain fluoroelastomers and certain bromine-containing compounds under conditions suitable for delivering cured parts possessing outstanding mechanical and sealing properties and incorporating suitable amounts of bromine-containing compounds, so that these cured parts, when submitted to wear/damage would release Br-containing compounds, which can easily detected using appropriate analytical techniques, so as to monitor and anticipate critical failures thereof.

19 Claims, No Drawings

METHOD OF MAKING CURED PARTS

CROSS-REFERENCE TO RELATED APPLICATIONS

This application is a U.S. national stage entry under 35 U.S.C. § 371 of International Application No. PCT/EP2018/057476 filed Mar. 23, 2018, which claims priority to European application No. 17164042.8, filed on Mar. 31, 2017, and to European application No. 17170781.3, filed on May 12, 2017. The entire contents of these applications are explicitly incorporated herein by this reference.

TECHNICAL FIELD

The invention pertains to a method of making cured parts having ability to interact with specific sensors in case of wear or damage, and to cured articles obtained therefrom, which are notably useful as smart seals.

BACKGROUND ART

Fluoroelastomers, and more specifically perfluoroelastomers, have long been used in a variety of applications that require excellent resistance to several rash conditions, including high temperature, chemical attack, and exposure to plasma, including in particular in the semi-conductors' manufacturing industry. Especially in this area, the possibility of monitoring wear and damages which may be incurred in sealing parts is an essential requirement for optimizing production, and avoiding wastes of manufactured semi-conductor goods out-of-spec because of undesirable contaminants or non-adapted manufacturing conditions.

Indeed, seals are mostly made of fluoroelastomers, which, in their pure form, cannot process signals and/or deliver signals. Several initiatives are being taken for investigating materials that make it possible to use seals as sensors or able to interact with sensors under specific conditions, without comprising the seal's original task.

One of the main challenge is to provide a seal able to recognize how worn it is, for instance. This self-monitoring is also known as "condition monitoring."

One exemplary solution has been described notably by Freudenberg (see press release dated 25 Apr. 2016, available in web-page: https://www.fst.com/press/2016/freudenberg-smart-seals, downloaded on Mar. 10, 2017); according to this document, a rod seal composed of a conductive elastomer including effective amount of conductive filler material and an insulating outer layer is provided, whereas the outer layer is the sealing lip in the seal. When an electrical circuit connects the rod and the housing wall, electricity can become a measurable variable. As the rod seal moves back and forth, the sealing lip abrades. If the conductive base material reaches the surface, the electrical circuit between the rod and the housing closes—a condition that a LED could signal.

Nevertheless, this solution requires the use of peripheral's (electric circuit) in direct contact with the seal to be monitored, which may be an impracticable solution in several assemblies.

In this area, there remains hence a continuous quest for cured parts expressing condition monitoring towards wear/structural damages, maintaining manufacturing costs at reasonable level, and without impairing primary role of the seal, and for methods of making the same.

DE 3823278 (NIPPON MEKTRON KK) 26 Jan. 1989 pertains to a fluorine-containing elastic copolymer comprising (a) about 30 to about 80 percent by mole of tetrafluoroethylene, (b) about 5 to about 60 percent by mole of perfluoro(lower alkyl vinyl ether) and (c) a perfluoroether compound represented by following general formula: $CF_2=CFOCF_2CFXOR_f$, wherein X: F or $-CF_3$ and $R_f$: $-C_nF_{2n+1}$, which copolymer is obtained by copolymerizing the (a) component, the (b) component and the (c) component in the presence of a radical polymerization initiator. This copolymer may comprise iodine or bromine, derived from a linear iodo- or bromo-containing compound used as chain transfer agent during copolymerization.

US 2004014900 (3M INNOVATIVE PROPERTIES CO) 22 Jan. 2004 discloses a curable composition comprising: (a) a fluoropolymer comprising interpolymerized units derived from (i) $CF_2=CF-R_f$, wherein $R_f$ is fluorine or a $C_1-C_8$ perfluoroalkyl, (ii) at least about 10 mole percent of a hydrogen-containing $C_2-C_9$ olefin, based on the total moles of said $CF_2=CFR_f$ and said olefin, (iii) an average of two or more bromine atoms including one or more terminal bromine atom(s) per fluoropolymer chain, (iv) optionally $CX_2=CX-R$, wherein each X is independently H, F, or Cl and R is a halogen or a $C_1-C_8$ alkyl or alkenyl group that may include one or more ether linkage(s), (v) optionally a bromine-containing cure site monomer;
(b) a peroxide curing agent; and
(c) a crosslinking co-agent.

U.S. Pat. No. 4,906,917 (US DEPARTMENT OF ENERGY [US]) Jun. 3, 1990 pertains to a method of monitoring the degradation of an elastomer, the method comprising the steps of: contacting a piezoelectric material having associated electrical contacts with the elastomer to form an oscillating system, the piezoelectric material and associated contacts being part of an oscillator circuit; causing the oscillator circuit to oscillate; measuring a parameter of the oscillator circuit; and relating changes in the parameter of the oscillator circuit to the degradation of the elastomer.

SUMMARY OF INVENTION

A first object of the invention is hence a method of making a cured shaped article [article (P)], said method comprising:
(i) providing a fluoroelastomer composition [composition (C)] comprising:
   at least one fluoroelastomer [fluoroelastomer (A)] comprising from 0.1 to 10.0% moles, with respect to total moles of recurring units of fluoroelastomer (A), of recurring units derived from at least one cure-site containing monomer having at least a nitrile group [monomer (CS-N)];
   at least one curing agent [agent (A)];
   at least one bromine-containing marker [marker (B)], selected from the group consisting of compounds comprising at least one aromatic ring and at least one bromine atom bound to a $sp^2$-hybridized aromatic carbon; and
(ii) molding the said composition (C) under heating for a time of at least 30 minutes at a temperature of at most 200° C.

The Applicant has surprisingly found that when processing the afore-mentioned curable compound, including a fluoroelastomer comprising nitrile cure sites, a curing system for the same, and a Br-containing aromatic marker, in the conditions as stipulated above, this compound can be cured so as to deliver cured shaped artiles maintaining chemically bound bromine atoms: cured shaped articles so obtained, when submitted to wear/damage would hence release Br-containing contaminants, which are solely originating from seals' damages as bromine atoms are generally absolutely not comprised in semi-conductors raw materials or final parts, and which can easily spotted via notably an on-line mass spectrometer, such as those which are routinely connected to semi-conductors' manufacture.

DETAILED DESCRIPTION OF THE INVENTION

The composition (C) comprises one or more than one agent (A), as above detailed.

The said agent (A) is an agent able to promote the cross-linking of the fluoroelastomer (A) through reaction with the cure sites of monomers (CS-N), as above described. The agent (A) maybe notably a compound possessing a plurality of groups having reactivity towards the nitrile groups of monomers (CS-N), as above described, and/or can be a compound activating catalytically the same nitrile groups of monomers (CS-N) to react among each other.

The choice of the curing agent (A) is not particularly limited, and one of ordinary skills in the art will select the most suitable curing agent (A) depending on the nature of the cure sites of the fluoroelastomer (A).

One or more than one agent (A) can be used in the composition of the present invention. Notably, one or more than one agent (A) may be selected among those possessing a plurality of groups having reactivity towards the nitrile groups of monomers (CS-N), as above described; and one or more than one agent (A) may be selected among those activating catalytically the same nitrile groups of monomers (CS-N) to react among each other, and one or more than one of these two types of agents (A) can be used alone or in combination in the composition of the present invention.

When the agent (A) is selected among compounds possessing catalytic activity towards activation of nitrile groups of monomers CS-N, as above described, the agent (A) is referred to as an agent ($A_{cat}$), and can be notably selected from the group consisting of:

- an organic ammonia-generating compound, that is to say a compound able to generate ammonia upon heating (e.g. in conditions such as those encountered during curing/post-cure);
- an organotin compound, such as notably allyl-propargyl-, triphenyl-, and allenyl-tin curatives, with tetraalkyl or tetraaryl tin compounds being preferred.

Agent ($A_{cat}$) is preferably selected from the group consisting of:

($A_{cat}$-1): (thio)urea compounds of formula (U) and salts thereof:

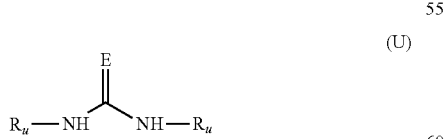

(U)

wherein E is O or S, preferably E is O, and each of $R_u$, equal to or different from each other, is independently selected from the group consisting of hydrogen and $C_1$-$C_6$ hydrocarbon groups (in particular $C_1$-$C_6$ alkyl groups); ($A_{cat}$-2): cyclic addition products of ammonia or primary amine and aldehyde;

($A_{cat}$-3): (thio)carbamates of formula (C):

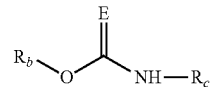

(C)

wherein E is oxygen or sulphur; $R_b$ is a $C_1$-$C_{36}$ hydrocarbon group, and $R_c$ is H or a $C_1$-$C_6$ alkyl group;

($A_{cat}$-4): ammonium salts of organic and inorganic acids, notably selected from the group consisting of (j) ammonium (preferably fluorine-containing) carboxylates; (jj) ammonium (preferably fluorine-containing) sulfonates; (jjj) ammonium (preferably fluorine alkyl group-containing) phosphates, phosphonates or sulfonates; (jv) ammonium salts of sulfuric acid, carbonic acid, nitric acid and phosphoric acid.

Among suitable agents ($A_{cat}$):

($A_{cat}$-1): (thio)urea compounds, as above detailed, are preferably selected from the group consisting of ($A_{cat}$-1-A) (thio)ureas of formula (U-2):

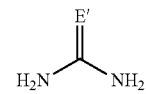

(U2)

wherein E' is O or S;

($A_{cat}$-2): cyclic addition products of ammonia or primary amine and aldehyde, as above detailed, are preferably selected from the group consisting of:

($A_{cat}$-2-A) cyclic aldehyde adducts trimers of formula (T):

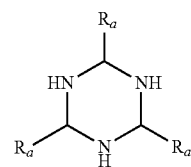

(T)

wherein each of $R_a$, equal to or different from each other, is selected from the group consisting of hydrogen and $C_1$-$C_6$ hydrocarbon groups (in particular $C_1$-$C_6$ alkyl groups);

($A_{cat}$-2-B) hexamethylene tetramine of formula:

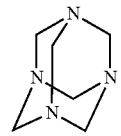

(which is known to be the result of addition of ammonia on formaldehyde);

($A_{cat}$-3): (thio)carbamates, as above detailed, are preferably selected from the group consisting of ($A_{cat}$-3-A) carbamates of formula (C-1):

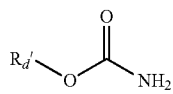

wherein R'$_d$ is a C$_1$-C$_{36}$ hydrocarbon group, preferably is a optionally substituted benzyl group.

Agents (A$_{cat}$) which have been found particularly useful in the composition of the present invention are the following:

(A$_{cat}$-1) Urea of formula:

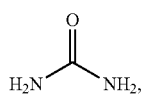

which is the preferred option in terms of costs/availability/reactivity;

(A$_{cat}$-2) Acetaldehyde ammonia trimer of formula:

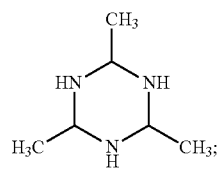

(A$_{cat}$-3) Hexamethylenetetramine of formula:

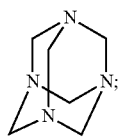

(A$_{cat}$-4) Benzyl carbamate of formula:

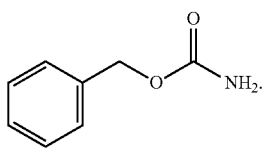 [SMILES: NC(=O)OCc1ccccc1]

When the agent (A) is selected among compounds possessing a plurality of groups having reactivity towards the nitrile groups of monomers (CS-N), as above described, the agent (A) is referred to as an agent (A$_{func}$), and can be notably selected from the group consisting of:

(A$_{func}$-1) bis-amino(thio)phenol compounds [aminophenol (AP)] of formula:

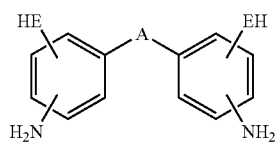

wherein:
A is a bond, —SO$_2$—, —O—, —C(O)—, or a (fluoro)alkyl of 1 to 10 carbon atoms (specifically a perfluoroalkyl of 1 to 10 carbon atoms, e.g. —C(CF$_3$)$_2$—);
each of E, equal of different at each occurrence, is oxygen or sulphur, preferably oxygen, and wherein the amino and -EH groups are interchangeably in ortho, meta or para positions with respect to the group A;

(A$_{func}$-2) aromatic tetraamine compounds [amine (TA)] of formula:

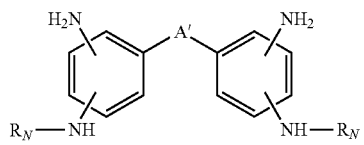

wherein:
A' is a bond, —SO$_2$—, —O—, —C(O)—, (fluoro)alkyl of 1 to 10 carbon atoms (specifically a perfluoroalkyl of 1 to 10 carbon atoms, e.g. —C(CF$_3$)$_2$—);
each of R$_N$, equal to or different from each other, is a hydrogen atom or a C$_1$-C$_{12}$ hydrocarbon group, preferably an aryl group; and
the amino groups are interchangeably in ortho, meta or para positions with respect to the group A', (A$_{func}$-3) bis-amidoxime/amidine/amidrazone compounds of formula:

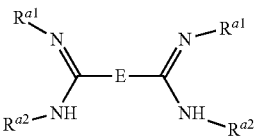

wherein R$_{a1}$ is —OH or —H, and R$_{a2}$ is H or NH$_2$, and E is a C$_1$-C$_{18}$ divalent group, optionally comprising fluorine atoms;

(A$_{func}$-4) bis-imidoylamidine compounds of formula:

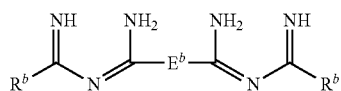

wherein E$^b$ is a C$_1$-C$_{18}$ divalent group, optionally comprising fluorine atoms, and R$^b$ is a C$_1$-C$_{12}$ group, optionally fluorinated.

Among bis-amidoxime/amidine/amidrazone compounds (A$_{func}$-3) as above detailed, mention can be notably made of:

(A$_{func}$-3-A): fluorinated bis-amidoxime compounds of formula:

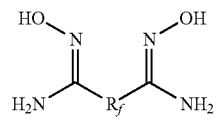

wherein Rf is a divalent fluorinated alkylidene group, preferably a group of formula —(CF$_2$)$_n$—, with n being 1 to 10, or wherein R$_f$ is a (per)fluorooxyalkylene group, preferably a group selected from —(CFX)$_p$(OCF$_2$CFX)$_n$(OCFX)$_m$O—(CFX)$_p$—, with X being F or —CF$_3$; n, m being zero or integers, with the proviso that n+m is from 1 to 100; and m being 1 or 2.

(A$_{func}$-3-B) aromatic bis-amidoxime compounds of formula:

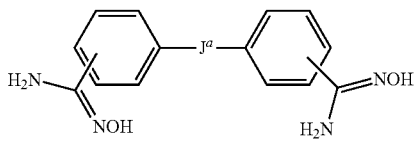

wherein J$^a$ is a bond, —SO$_2$—, —O—, —C(O)—, (fluoro) alkyl of 1 to 10 carbon atoms (specifically a perfluoroalkyl of 1 to 10 carbon atoms, e.g. —C(CF$_3$)$_2$—);

(A$_{func}$-3-C): fluorinated bis-amidrazone compounds of formula:

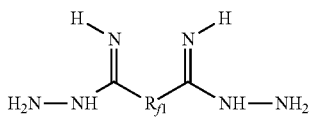

wherein R$_f$ is a divalent fluorinated alkylidene group, preferably a group of formula —(CF$_2$)$_n$—, with n being 1 to 10, or wherein R$_f$ is a (per)fluorooxyalkylene group, preferably a group selected from —(CFX)$_p$(OCF$_2$CFX)$_n$(OCFX)$_m$O—(CFX)$_p$—, with X being F or —CF$_3$; n, m being zero or integers, with the provisio that n+m is from 1 to 100; and m being 1 or 2.

(A$_{func}$-3-D) aromatic bis-amidrazone compounds of formula:

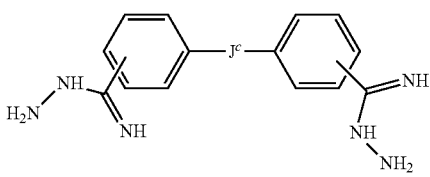

wherein J$^c$ is a bond, —SO$_2$—, —O—, —C(O)—, (fluoro) alkyl of 1 to 10 carbon atoms (specifically a perfluoroalkyl of 1 to 10 carbon atoms, e.g. —C(CF$_3$)$_2$—).

According to certain preferred embodiment's, agent (A) is an aminophenol (AP), as above detailed.

The aminophenol (AP) can be selected from the group consisting of 4,4'-[2,2,2-trifluoro-1-(trifluoromethyl)-ethylidene]bis(2-aminophenol); 4,4'-sulfonylbis(2-aminophenol); 3,3'-diaminobenzidine, 3,3',4,4'-tetraaminobenzophenone.

Particularly preferred aminophenol (AP) is 4,4'-[2,2,2-trifluoro-1-(trifluoromethyl)-ethylidene]bis(2-aminophenol), otherwise known as bis-aminophenol AF, having formula:

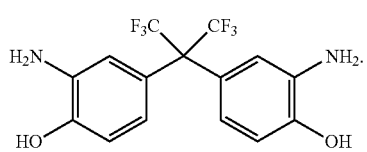 [SMILES: Nc1cc(C(c2ccc(O)c(N)c2)(C(F)(F)F)C(F)(F)F)ccc1O]

The composition (C) comprises one or more than one marker (B), as above detailed, i.e. a compound comprising at least one aromatic ring and at least one bromine atom bound to a sp$^2$-hybridized aromatic carbon.

Without being bound by this theory, the Applicant has surprisingly found that marker (B), as above detailed, in the peculiar conditions recited above (at least 30 minutes at a temperature of at most 200° C.) which have been found effective for achieving substantial curing, does not detrimentally affect curing efficiency nor undergo any significant evaporative loss or decomposition, hence ensuring in so obtained final rubber parts the presence of bromine-containing compounds, which can be easily detected through different analytical techniques, including notably mass spectrometry, if and when released in a certain environment, because e.g. of wear and/or material decomposition for whichever reason.

This is of particular advantage especially in semiconductors' manufacture, whereas fluoroelastomers are widely used as sealing materials, and wherein, from one side, conditions are extremely harsh and severe, including e.g. plasma radiation, HF and other etching gases exposure, and yet wherein extreme cleanness and absence of contaminants of whichever type, including wastes from damaged equipment's seals, is mandatory to meet quality standards.

As said, marker (B) comprises at least one bromine atom. Marker (B) may comprise one or more than one bromine atoms.

Indeed, the Applicant has found that when the said at least one bromine atom of marker (B) is bound to an aromatic moiety through said bond to an annular aromatic sp$^2$ hybridized carbon, thermal resistance of the said Br—C bond is enhanced, so that the release of bromine from composition (C) and/or from cured parts derived therefrom mainly and substantially intervene because of critical failure of cured parts derived therefrom, and does not occur during the curing method, provided that the processing conditions stipulated above are respected.

As said, marker (B) comprises at least one aromatic ring. Marker (B) may comprise one or more than one aromatic rings; when marker (B) comprises more than one aromatic ring, the said aromatic rings may be condensed, or may be connected through a bond or through whichever type of bridging group.

Marker (B) may comprise fluorine atoms.

Marker (B) generally complies with formula (B-1) below:

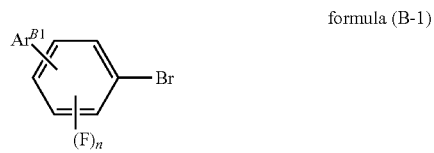

formula (B-1)

whereas Ar$_{B1}$ is an aromatic group, possibly comprising fluorine atoms; n is zero or is an integer of 1 to 4.

Among preferred markers (B), mention can be notably made of 4,4'-dibromooctafluorobiphenyl of formula:

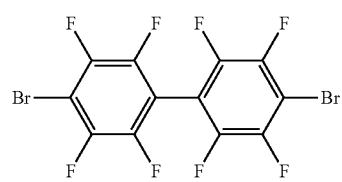

and 4-bromobiphenyl of formula:

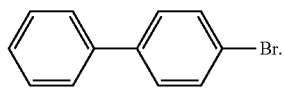

The composition (C) generally comprises:
marker (B), as above detailed, in an amount of generally ranging from 0.10 to 10 phr, preferably of 0.25 to 6 phr, with respect to fluoroelastomer (A); and
agent (A), as above detailed, in an amount of ranging from 0.10 to 10 phr, preferably of 0.25 to 5 phr, with respect to fluoroelastomer (A).

The composition (C) comprises one or more than one fluoroelastomer (A), as above detailed.

For the purposes of this invention, the term "(per)fluoroelastomer" [fluoroelastomer (A)] is intended to designate a fluoropolymer resin serving as a base constituent for obtaining a true elastomer, said fluoropolymer resin comprising more than 10% wt, preferably more than 30% wt, of recurring units derived from at least one ethylenically unsaturated monomer comprising at least one fluorine atom (hereafter, (per)fluorinated monomer) and, optionally, recurring units derived from at least one ethylenically unsaturated monomer free from fluorine atom (hereafter, hydrogenated monomer).

True elastomers are defined by the ASTM, Special Technical Bulletin, No. 184 standard as materials capable of being stretched, at room temperature, to twice their intrinsic length and which, once they have been released after holding them under tension for 5 minutes, return to within 10% of their initial length in the same time.

Generally fluoroelastomer (A) comprises recurring units derived from at least one (per)fluorinated monomer, in addition to recurring units derived from monomer (CS-N), as above detailed, wherein said (per)fluorinated monomer is generally selected from the group consisting of:
$C_2$-$C_8$ fluoro- and/or perfluoroolefins, such as tetrafluoroethylene (TFE), hexafluoropropene (HFP), pentafluoropropylene, and hexafluoroisobutylene;
$C_2$-$C_8$ hydrogenated monofluoroolefins, such as vinyl fluoride; 1,2-difluoroethylene, vinylidene fluoride (VDF) and trifluoroethylene (TrFE);
(per)fluoroalkylethylenes complying with formula $CH_2$=$CH$—$R_{f0}$, in which $R_{f0}$ is a $C_1$-$C_6$ (per)fluoroalkyl or a $C_1$-$C_6$ (per)fluorooxyalkyl having one or more ether groups;
chloro- and/or bromo- and/or iodo-$C_2$-$C_6$ fluoroolefins, like chlorotrifluoroethylene (CTFE);
fluoroalkylvinylethers complying with formula $CF_2$=$CFOR_{f1}$ in which $R_{f1}$ is a $C_1$-$C_6$ fluoro- or perfluoroalkyl, e.g. —$CF_3$, —$C_2F_5$, —$C_3F_7$;
hydrofluoroalkylvinylethers complying with formula $CH_2$=$CFOR_{f1}$ in which $R_{f1}$ is a $C_1$-$C_6$ fluoro- or perfluoroalkyl, e.g. —$CF_3$, —$C_2F_5$, —$C_3F_7$;
fluoro-oxyalkylvinylethers complying with formula $CF_2$=$CFOX_0$, in which $X_0$ is a $C_1$-$C_{12}$ oxyalkyl, or a $C_1$-$C_{12}$ (per)fluorooxyalkyl having one or more ether groups; in particular (per)fluoro-methoxy-vinylethers complying with formula $CF_2$=$CFOCF_2OR_{f2}$ in which $R_{f2}$ is a $C_1$-$C_6$ fluoro- or perfluoroalkyl, e.g. —$CF_3$, —$C_2F_5$, —$C_3F_7$ or a $C_1$-$C_6$ (per)fluorooxyalkyl having one or more ether groups, like —$C_2F_5$—O—$CF_3$;
functional fluoro-alkylvinylethers complying with formula $CF_2$=$CFOY_0$, in which $Y_0$ is a $C_1$-$C_{12}$ alkyl or (per)fluoroalkyl, or a $C_1$-$C_{12}$ oxyalkyl or a $C_1$-$C_{12}$ (per)fluorooxyalkyl, said $Y_0$ group comprising a carboxylic or sulfonic acid group, in its acid, acid halide or salt form;
(per)fluorodioxoles, of formula:

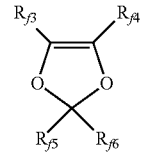

wherein each of $R_{f3}$, $R_{f4}$, $R_{f5}$, $R_{f6}$, equal to or different from each other, is independently a fluorine atom, a $C_1$-$C_6$ fluoro- or per(halo)fluoroalkyl, optionally comprising one or more oxygen atom, e.g. —$CF_3$, —$C_2F_5$, —$C_3F_7$, —$OCF_3$, —$OCF_2CF_2OCF_3$.

Examples of hydrogenated monomers are notably hydrogenated alpha-olefins, including ethylene, propylene, 1-butene, diene monomers, styrene monomers, alpha-olefins being typically used.

Fluoroelastomers (A) are in general amorphous products or products having a low degree of crystallinity (crystalline phase less than 20% by volume) and a glass transition temperature ($T_g$) below room temperature. In most cases, the fluoroelastomer (A) has advantageously a $T_g$ below 10° C., preferably below 5° C., more preferably 0° C.

The fluoroelastomer (A) is preferably selected among:
(1) VDF-based copolymers, in which VDF is copolymerized with monomer (CS-N), as above detailed, and at least one additional comonomer selected from the group consisting of:
(a) $C_2$-$C_8$ perfluoroolefins, such as tetrafluoroethylene (TFE), hexafluoropropylene (HFP);
(b) hydrogen-containing $C_2$-$C_8$ olefins, such as vinyl fluoride (VF), trifluoroethylene (TrFE), hexafluoroisobutene (HFIB), perfluoroalkyl ethylenes of formula $CH_2$=$CH$—$R_f$, wherein $R_f$ is a $C_1$-$C_6$ perfluoroalkyl group;
(c) $C_2$-$C_8$ fluoroolefins comprising at least one of iodine, chlorine and bromine, such as chlorotrifluoroethylene (CTFE);
(d) (per)fluoroalkylvinylethers (PAVE) of formula $CF_2$=$CFOR_f$, wherein $R_f$ is a $C_1$-$C_6$ (per)fluoroalkyl group, preferably $CF_3$, $C_2F_5$, $C_3F_7$;
(e) (per)fluoro-oxy-alkylvinylethers of formula $CF_2$=$CFOX$, wherein X is a $C_1$-$C_{12}$ ((per)fluoro)-oxyalkyl comprising catenary oxygen atoms, e.g. the perfluoro-2-propoxypropyl group;
(f) (per)fluorodioxoles having formula:

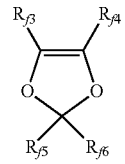

wherein each of $R_{f3}$, $R_{f4}$, $R_{f5}$, $R_{f6}$, equal to or different from each other, is independently selected from the group consisting of fluorine atom and $C_1$-$C_6$ (per)fluoroalkyl groups, optionally comprising one or more than one oxygen atom, such as notably —$CF_3$, —$C_2F_5$, —$C_3F_7$, —$OCF_3$, —$OCF_2CF_2OCF_3$; preferably, perfluorodioxoles;

(g) (per)fluoro-methoxy-vinylethers (MOVE, hereinafter) having formula: $CF_2=CFOCF_2OR_{f2}$
wherein $R_{f2}$ is selected from the group consisting of $C_1$-$C_6$ (per)fluoroalkyls; $C_5$-$C_6$ cyclic (per)fluoroalkyls; and $C_2$-$C_6$ (per)fluorooxyalkyls, comprising at least one catenary oxygen atom; $R_{f2}$ is preferably —$CF_2CF_3$ (MOVE1); —$CF_2CF_2OCF_3$ (MOVE2); or —$CF_3$ (MOVE3);
(h) $C_2$-$C_8$ non-fluorinated olefins (OI), for example ethylene and propylene; and
(2) TFE-based copolymers, in which TFE is copolymerized with monomer (CS-N), as above detailed, and at least one additional comonomer selected from the group consisting of (c), (d), (e), (g), (h) and (i) as above detailed.

Fluoroelastomer (A) is generally selected among TFE-based copolymers, as above detailed.

Optionally, fluoroelastomer (A) of the present invention may also comprises recurring units derived from a bis-olefin [bis-olefin (OF)] having general formula:

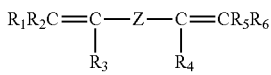

wherein $R_1$, $R_2$, $R_3$, $R_4$, $R_5$ and $R_6$, equal or different from each other, are H or $C_1$-$C_5$ alkyl; Z is a linear or branched $C_1$-$C_{18}$ (hydro)carbon radical (including alkylene or cycloalkylene radical), optionally containing oxygen atoms, preferably at least partially fluorinated, or a (per)fluoro(poly)oxyalkylene radical comprising one or more catenary ethereal bonds.

The bis-olefin (OF) is preferably selected from the group consisting of those complying with formulae (OF-1), (OF-2) and (OF-3):
(OF-1)

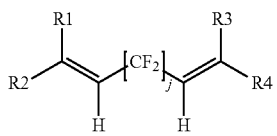

wherein j is an integer between 2 and 10, preferably between 4 and 8, and $R_1$, $R_2$, $R_3$, $R_4$, equal or different from each other, are H, F or $C_{1-5}$ alkyl or (per)fluoroalkyl group;
(OF-2)

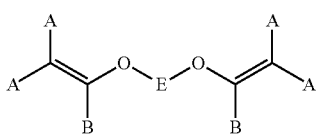

wherein each of A, equal or different from each other and at each occurrence, is independently selected from F, Cl, and H; each of B, equal or different from each other and at each occurrence, is independently selected from F, Cl, H and $OR_B$, wherein $R_B$ is a branched or straight chain alkyl radical which can be partially, substantially or completely fluorinated or chlorinated; E is a divalent group having 2 to 10 carbon atom, optionally fluorinated, which may be inserted with ether linkages; preferably E is a —$(CF_2)_m$— group, with m being an integer from 3 to 5; a preferred bis-olefin of (OF-2) type is $F_2C=CF$—O—$(CF_2)_5$—O—$CF=CF_2$.
(OF-3)

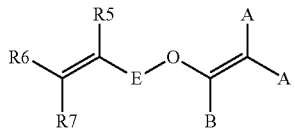

wherein E, A and B have the same meaning as above defined; R5, R6, R7, equal or different from each other, are H, F or $C_{1-5}$ alkyl or (per)fluoroalkyl group.

Among cure-site containing monomers of type (CS-N), as above detailed, comprised in fluoroelastomer (A), preferred monomers are (per)fluorinated and are especially those selected from the group consisting of:
(CS-N1) perfluorovinyl ethers containing nitrile groups of formula $CF_2=CF$—$(OCF_2CFX^{CN})_m$—O—$(CF_2)_n$—CN, with $X^{CN}$ being F or $CF_3$, m being 0, 1, 2, 3 or 4; n being an integer from 1 to 12;
(CS-N2) perfluorovinyl ethers containing nitrile groups of formula $CF_2=CF$—$(OCF_2CFX^{CN})_{m'}$—O—$CF_2CF(CF_3)$—CN, with $X^{CN}$ being F or $CF_3$, m' being 0, 1, 2, 3 or 4.

Specific examples of cure-site containing monomers of type CS-N1 and CS-N2 suitable to the purposes of the present invention are notably those described in U.S. Pat. No. 4,281,092 (DU PONT) 28 Jul. 1981, U.S. Pat. No. 4,281,092 (DU PONT) 28 Jul. 1981, U.S. Pat. No. 5,447,993 (DU PONT) May 9, 1995 and U.S. Pat. No. 5,789,489 (DU PONT) Apr. 8, 1998.

Preferred cure-site monomer (CS-N) is perfluoro(8-cyano-5-methyl-3,6-dioxa-1-octene) of formula: $CF_2=CF$—O—$CF_2$—$CF(CF_3)$—O—$CF_2$—$CF_2$—CN (8-CNVE).

Exemplary preferred fluoroelastomers (A) which can be used in the composition of the present invention are those having following monomers composition (in mol %, with respect to the total moles of recurring units):
(i) tetrafluoroethylene (TFE): 50-80%; (per)fluoroalkylvinylethers (PAVE): 15-50%; monomer (CS-N): 0.1-10%; bis-olefin (OF): 0-5%;
(ii) tetrafluoroethylene (TFE): 20-70%; (per)fluoromethoxy-vinylethers (MOVE): 25-75%; (per)fluoroalkylvinylethers (PAVE): 0-50%; monomer (CS-N) 0.1-10%; bis-olefin (OF): 0-5%.

The composition (C) may further additionally comprise ingredients which maybe commonly used for curing of fluoroelastomers; more specifically, composition (C) may generally further comprise
(a) one or more than one metallic basic compound, in amounts generally of from 0.5 to 15 phr, and preferably of from 1 to 10 phr, relative to 100 weight parts of fluoroelastomer (A); metallic basic compounds are generally selected from the group consisting of (j) oxides or hydroxides of divalent metals, for instance oxides or hydroxides of Mg, Zn, Ca or Pb, and (jj) metal salts of a weak acid, for instance Ba, Na, K, Pb, Ca stearates, benzoates, carbonates, oxalates or phosphites;
(b) one or more than one acid acceptor which is not a metallic basic compound, in amounts generally of from 0.5 to 15 phr, and preferably of from 1 to 10 phr, relative to 100 weight parts of fluoroelastomer (A); these acid acceptors are generally selected from nitrogen-containing organic compounds, such as 1,8-bis(dimethylamino)naphthalene, octadecylamine, etc., as notably described in EP 708797 A (DU PONT) Jan. 5, 1996;
(c) other conventional additives, such as fillers, thickeners, pigments, antioxidants, stabilizers, processing aids, and the like.

As said, the invention pertains to a method of making a cured shaped article [article (P)], said method comprising notably a step (ii) of molding the composition (C), as detailed above, under heating for a time of at least 30 minutes at a temperature of at most 200° C.

The expression "molding" when used in connection with composition (C) is hereby intended to encompass all methods of fabricating/shaping articles, starting from the said composition (C), including any post-treatment or further processing, which would finally deliver the cured shaped article, as above detailed.

The step of molding can include a step of injection moulding, compression moulding, extrusion moulding, coating, screen printing, forming-in-place, calendaring the composition (C) into the desired shaped article. The said shaped article is advantageously subjected to vulcanization (curing) during the processing itself and/or in a subsequent step (post-treatment or post-cure), advantageously transforming the relatively soft, weak, fluoroelastomeric uncured composition into a finished article made of non-tacky, strong, insoluble, chemically and thermally resistant cured fluoroelastomer material.

It remains nevertheless a requirement of the method of the present invention to perform said molding under heating at a temperature of at most 200° C., preferably of at most 195° C., more preferably of at most 190° C., and even more preferably of at most 185° C. and/or at a temperature of at least 160° C., preferably at least 165° C., more preferably at least 170° C.

Said heating, in the molding step of the method of the invention is pursued for a duration of at least 30 minutes, preferably of at least 45 minutes, more preferably at least one hour.

There's no particular upper limit which has to be imposed on the duration of the heating step; one of ordinary skills in the art will ensure that the duration chosen will be consistent with general industry requirements to deliver appropriate manufacturing throughput of shaped articles (P) of constant and appropriate quality. Hence, said heating, in the molding step of the method of the invention is pursued for a duration generally of less than 16 hours, preferably less than 14 hours, preferably less than 12 hours.

Yet, the invention pertains to cured shaped articles (P) obtained from the composition (C) using the method, as above detailed. These cured articles may be sealing articles, including O(square)-rings, packings, gaskets, diaphragms, shaft seals, valve stem seals, piston rings, crankshaft seals, cam shaft seals, and oil seals or maybe piping and tubings, in particular flexible hoses or other items, including conduits for delivery of hydrocarbon fluids and fuels.

Further in addition, the invention pertains to a method for detecting wear/failures in cured shaped articles (P), as above detailed, said method comprising monitoring release of bromine-containing compounds from the same.

Techniques for monitoring release of bromine-containing compounds are not particularly limited, and can be based on standard analytical techniques. Mass spectrometry is particularly adapted for detecting bromine-containing compounds, thanks to the peculiar double peak associated to ions losing a bromine atom.

Should the disclosure of any of the patents, patent applications, and publications that are incorporated herein by reference conflict with the present description to the extent that it might render a term unclear, the present description shall take precedence.

The present invention will be now described in more detail with reference to the following examples, whose purpose is merely illustrative and not limitative of the scope of the invention.

Raw Materials

Bis-aminophenol AF (BOAP, herein after) was supplied from Apollo Scientific and used as received.

4,4'-dibromo-octafluorobiphenyl (DBOFBP, herein after) was supplied from Apollo Scientific and used as received.

4-bromobiphenyl (BBP, herein after) was supplied from Sigma Aldrich and used as received.

Preparative Example 1—Manufacture of an Elastomer Comprising Nitrile Groups

In a 5 litres reactor equipped with a mechanical stirrer operating at 630 rpm, 3.1 l of demineralized water and 31 ml of a microemulsion, previously obtained by mixing 7.4 ml of a perfluoropolyoxyalkylene having acidic end groups of formula: $CF_2ClO(CF_2—CF(CF_3)O)_n(CF_2O)_mCF_2COOH$, wherein n/m=10, having average molecular weight of 600, 1.9 ml of a 30% v/v $NH_4OH$ aqueous solution, 17.4 ml of demineralised water and 4.3 ml of GALDEN® D02 perfluoropolyether of formula: $CF_3O(CF_2CF(CF_3)O)_n(CF_2O)_mCF_3$ with n/m=20, having average molecular weight of 450, were introduced.

The reactor was heated and maintained at a set-point temperature of 80° C.; a mixture of tetrafluoroethylene (TFE) (35% moles) and perfluoromethylvinylether (MVE) (64.3% moles) and ethane (0.7% moles, chain transfer agent) was then added to reach a final pressure of 21 bar (2.1 MPa). 0.31 g of ammonium persulfate (APS) as initiator were then introduced. Pressure was maintained at set-point of 21 bar by continuous feeding of a gaseous mixture of TFE (57.5% moles) and MVE (42.5% moles) up to a total of 1350 g, and 129 g of 8-CNVE in 20 portions each 5% increase in conversion, starting from the beginning of the polymerization, were fed to the reactor. Moreover, 0.16 g of APS at 15%, 40% and 55% conversion of gaseous mixture, were introduced. Then the reactor was cooled, vented and the latex recovered. The latex was coagulated with nitric acid as a coagulation agent, and the polymer separated from the aqueous phase, washed with demineralised water and dried in a convection oven at 120° C. for 24 hours.

The composition of the obtained polymer from NMR analysis was found to be: TFE 60.8% mol, MVE 38.0% mol, 8-CNVE 1.2% mol, and the Mooney viscosity at 121° C. is 50 MU.

General Compounding and Curing Procedure

The fluoroelastomer of preparative Ex. 1 was compounded with the ingredients as detailed below in a two rolls open mill. Plaques were cured in a pressed mould in conditions detailed in Table below and, for comparative purposes, post-treated in an air circulating oven, as below detailed.

Cure behaviour was characterized by Moving Die Rheometer (MDR), at 170° C., by determining the following properties:

$M_L$=Minimum torque (lb×in)
$M_H$=Maximum torque (lb×in)
$t_{S2}$=Scorch time, time for two units rise from $M_L$ (sec);
$t_{02}$=Time to 2% state of cure (sec);

$t_{50}$=Time to 50% state of cure (sec);
$t_{90}$=Time to 90% state of cure (sec);
$t_{95}$=Time to 95% state of cure (sec).

The tensile properties have been determined on specimens punched out from the plaques, according to the ASTM D 412 C Standard.
TS is the tensile strength in MPa;
$M_{50}$ is the modulus in MPa at an elongation of 50%;
$M_{100}$ is the modulus in MPa at an elongation of 100%;
E.B. is the elongation at break in %.

Compression set (CS) values have been determined on O-rings (#214 class) according to the ASTM D 395-B method at a temperature of 200° C.; values in the table are the average of determinations made on 4 specimens.

Data comprised in Table below demonstrate that the method of making cured shaped articles according to the invention is effective in substantially retaining bromine compounds in the cured part.

Mechanical and Sealing Properties Determination

Data below, recollecting mechanical and sealing properties for cured parts obtained as above detailed, well demonstrate that the method of the invention delivers cured shaped parts possessing all outstanding properties of cured fluoroelastomer materials.

TABLE 1

| Ingredient | | Ex. 2 | Ex. 3 | Ex. 4 | Ex. 5C | Ex. 6C | Ex. 7C |
|---|---|---|---|---|---|---|---|
| FKM from Ex. 1 | wt parts | 100 | 100 | 100 | 100 | — | — |
| FKM Ref.(*) | wt parts | — | — | — | — | 100 | 100 |
| BOAP | phr | 0.70 | 0.70 | 0.70 | 0.70 | — | — |
| DBOFBP | phr | 1.00 | — | 5.00 | 5.00 | 5.00 | — |
| BBP | phr | — | 5.00 | — | — | — | 5.00 |
| Bis-olefin(#) | phr | — | — | — | — | 1.50 | 1.50 |
| Peroxide($) | phr | — | — | — | — | 1.00 | 1.00 |

(*)FKM Ref. is a iodine-containing peroxide curable perfluoroelastomer commercially available from Solvay Specialty Polymers Italy SpA under brand name TECNOFLON® 95HT;
(#)Bis-Olefin: of formula $CH_2=CH-(CF_2)_6-CH=CH_2$;
($)Peroxide: neat 2,5-dimethyl-2,5-di-t-butyl-peroxy-hexane, commercially available from Arkema under tradename Luperox® 101;

TABLE 2

| Sample | | Ex. 2 | Ex. 3 | Ex. 4 | Ex. 5C | Ex. 6C | Ex. 7C |
|---|---|---|---|---|---|---|---|
| $M_L$ | (Nxm) | 0.7 | 0.7 | 0.7 | 0.7 | 0.9 | 0.9 |
| $M_H$ | (Nxm) | 15.3 | 15.6 | 15.5 | 15.5 | 11.2 | 8.4 |
| $t_{s2}$ | (s) | 296.0 | 301.0 | 298.0 | 298.0 | 60.0 | 95.0 |
| $t_{02}$ | (s) | 118.0 | 121.0 | 126.0 | 126.0 | 37.0 | 42.0 |
| $t_{50}$ | (s) | 480.0 | 475.0 | 492.0 | 492.0 | 90.0 | 139.0 |
| $t_{90}$ | (s) | 1180.0 | 1059.0 | 1168.0 | 1168.0 | 206.0 | 310.0 |
| $t_{95}$ | (s) | 1414.0 | 1523.0 | 1259.0 | 1259.0 | 303.0 | 386.0 |
| Molding Conditions | | | | | | | |
| Time and T in the press | | 2 hours at 180° C. | | 20 min at 170° C. | | 5 min at 170° C. | |
| Post-cure conditions in air oven | | | | | | | |
| Conditions | | No post-cure | | (8 + 16 h) at 290° C. | | | |

Bromine Content Determination

Content of Br was determined by XRF (i) after compounding the elastomer with the ingredients listed in table 1, (ii) after curing/molding; (iii) after post-cure at 290° C., to the sake of comparison, in conditions as detailed above. Results are summarized in the following table.

TABLE 3

| Sample | Ex. 2 | Ex. 3 | Ex. 4 | Ex. 5C | Ex. 6C | Ex. 7C |
|---|---|---|---|---|---|---|
| Br content after compounding | | | | | | |
| Br (% wt) | 0.35 | 1.43 | 1.74 | 1.74 | 1.74 | 1.48 |
| Br content after moulding | | | | | | |
| Br (% wt) | 0.35 | 1.37 | 1.66 | 1.65 | 1.61 | 0.4 |
| Br content after post-cure | | | | | | |
| Br (% wt) | N.A.(*) | 0 | 0 | 0 | | |

(*)N.A. = not applicable; cured parts obtained from moulding, with no additional post-cure.

TABLE 4

| Property | | Ex. 2 | Ex. 3 | Ex. 4 | Ex. 5C | Ex. 6C | Ex. 7C |
|---|---|---|---|---|---|---|---|
| TS | (MPa) | 8.2 | 8.4 | 8.3 | 8.5 | 11.4 | 9.1 |
| $M_{50}$ | (MPa) | 1.0 | 1.0 | 1.1 | 1.2 | 0.9 | 0.9 |
| $K_{100}$ | (MPa) | 1.8 | 1.9 | 2.0 | 1.8 | 1.6 | 1.5 |
| E.B. | (%) | 196 | 187 | 185 | 187 | 254 | 274 |
| Hardness | (Sh A) | 57 | 57 | 57 | 57 | 56 | 56 |
| C-Set(*) | (%) | 10 | 9 | 15 | 8 | 16 | 18 |

(*)C-Set: 70 h @ 200° C.

The invention claimed is:
1. A method of making a cured shaped article [article (P)], said method comprising:
   molding a composition (C) under heating for a time of at least 30 minutes at a temperature of at most 200° C., wherein composition (C) is a fluoroelastomer composition comprising:
      at least one fluoroelastomer (A) comprising from 0.1 to 10.0% moles, with respect to total moles of recurring units of fluoroelastomer (A), of recurring units derived from at least one cure-site containing monomer having at least a nitrile group [monomer (CS-N)];
      at least one curing agent [agent (A)]; and
      at least one bromine-containing marker [marker (B)], wherein marker (B) complies with formula (B-1) below:

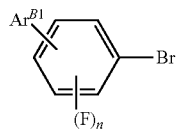

formula (B-1)

wherein $Ar^{B1}$ is an aromatic group, optionally comprising fluorine atoms; and n is zero or is an integer of 1 to 4.

2. The method according to claim 1, wherein the agent (A) is selected from compounds possessing catalytic activity towards activation of nitrile groups of monomer (CS-N), and wherein the agent (A) is referred to as an agent ($A_{cat}$), and is selected from the group consisting of:
an organic ammonia-generating compound, able to generate ammonia upon heating; and
an organotin compound.

3. The method according to claim 2, wherein the agent ($A_{cat}$) is selected from the group consisting of:
($A_{cat}$-1): (thio)urea compounds of formula (U) and salts thereof:

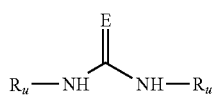

(U)

wherein E is O or S, and each of $R_u$, equal to or different from each other, is independently selected from the group consisting of hydrogen and $C_1$-$C_6$ hydrocarbon groups;
($A_{cat}$-2): cyclic addition products of ammonia or primary amine and aldehyde;
($A_{cat}$-3): (thio)carbamates of formula (C):

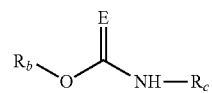

(C)

wherein E is oxygen or sulphur; $R_b$ is a $C_1$-$C_{36}$ hydrocarbon group, and $R_c$ is H or a $C_1$-$C_6$ alkyl group; and
($A_{cat}$-4): ammonium salts of organic and inorganic acids.

4. The method according to claim 3, wherein agent ($A_{cat}$) is selected from the group consisting of:
($A_{cat}$-1-A) (thio)ureas of formula (U-2):

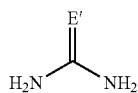

(U2)

wherein E' is O or S;
($A_{cat}$-2-A) cyclic aldehyde adducts trimers of formula (T):

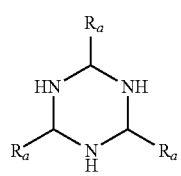

(T)

wherein each of $R_a$, equal to or different from each other, is selected from the group consisting of hydrogen and $C_1$-$C_6$ hydrocarbon groups;

($A_{cat}$-2-B) hexamethylene tetramine of formula:

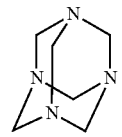

($A_{cat}$-3-A) carbamates of formula (C-1):

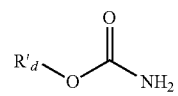

(C-1)

wherein $R'_d$ is a $C_1$-$C_{36}$ hydrocarbon group.

5. The method according to claim 3, wherein the agent ($A_{cat}$-4) is selected from the group consisting of (j) ammonium carboxylates optionally containing fluorine; (jj) ammonium sulfonates optionally containing fluorine; (jjj) ammonium phosphates optionally containing one or more fluorine-alkyl groups, phosphonates or sulfonates; (jv) ammonium salts of sulfuric acid, carbonic acid, nitric acid and phosphoric acid.

6. The method according to claim 2, wherein the organotin compound is selected from the group consisting of allyl-propargyl-, triphenyl-, and allenyl-tin curatives, and tetraalkyl or tetraaryl tin compounds.

7. The method of claim 1, wherein the agent (A) is selected from compounds possessing a plurality of groups having reactivity towards the nitrile groups of monomer (CS-N) and wherein the agent (A) is referred to as an agent ($A_{func}$), and is selected from the group consisting of:
($A_{func}$-1) bis-amino(thio)phenol compounds [aminophenol (AP)] of formula:

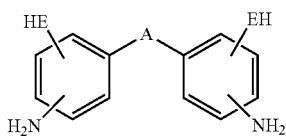

wherein:
A is a bond, —$SO_2$—, —O—, —C(O)—, or a (fluoro)alkyl of 1 to 10 carbon atoms;
each of E, equal of different at each occurrence, is oxygen or sulphur, and wherein the amino and -EH groups are interchangeably in ortho, meta or para positions with respect to the group A;
($A_{func}$-2) aromatic tetraamine compounds [amine (TA)] of formula:

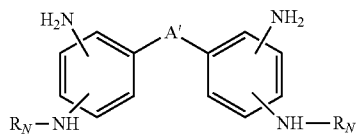

wherein:
A' is a bond, —$SO_2$—, —O—, —C(O)—, or a (fluoro)alkyl of 1 to 10 carbon atoms;

each of $R_N$, equal to or different from each other, is a hydrogen atom or a $C_1$-$C_{12}$ hydrocarbon group; and the amino groups are interchangeably in ortho, meta or para positions with respect to the group A', ($A_{func}$-3)'bis-amidoxime/amidine/amidrazone compounds of formula:

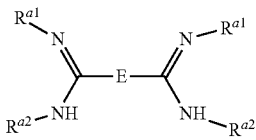

wherein $R_{a1}$ is —OH or —H, and $R_{a2}$ is H or $NH_2$, and E is a $C_1$-$C_{18}$ divalent group, optionally comprising fluorine atoms; and ($A_{func}$-4) bis-imidoylamidine compounds of formula:

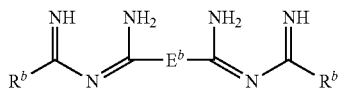

wherein $E^b$ is a $C_1$-$C_{18}$ divalent group, optionally comprising fluorine atoms, and $R^b$ is a $C_1$-$C_{12}$ group, optionally fluorinated.

8. The method of claim 5, wherein the agent ($A_{func}$) is 4,4'-[2,2,2-trifluoro-1-(trifluoromethyl)-ethylidene]bis(2-aminophenol), otherwise known as bis-aminophenol AF, having formula:

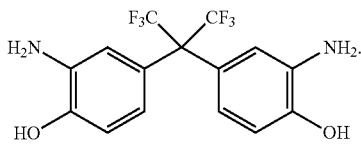 [SMILES: Nc1cc(C(c2ccc(O)c(N)c2)(C(F)(F)F)C(F)(F)F)ccc1O]

9. The method according to claim 7, wherein
agent (A) is agent ($A_{func}$-1), A is —C(CF$_3$)$_2$— and each of E, equal to or different at each occurrence, is oxygen; or
agent (A) is agent ($A_{func}$-2), A' is —C(CF$_3$)$_2$—, and each of $R_N$, equal to or different from each other, is an aryl group.

10. The method of claim 1, wherein marker (B) is selected from the group consisting of 4,4'-dibromooctafluorobiphenyl of formula:

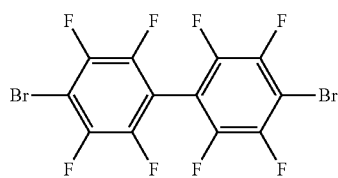 [SMILES: Fc1c(F)c(-c2c(F)c(F)c(Br)c(F)c2F)c(F)c(F)c1Br]

and 4-bromobiphenyl of formula:

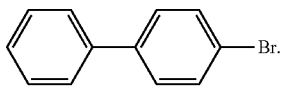 [SMILES: Brc1ccc(-c2ccccc2)cc1]

11. The method according to claim 1, wherein composition (C) comprises:
marker (B), in an amount ranging from 0.10 to 10 phr, with respect to fluoroelastomer (A); and/or
agent (A), in an amount ranging from 0.10 to 10 phr, with respect to fluoroelastomer (A).

12. The method according to claim 11, wherein composition (C) comprises:
marker (B), in an amount ranging from 0.25 to 6 phr, with respect to fluoroelastomer (A); and/or
agent (A), in an amount ranging from 0.25 to 5 phr, with respect to fluoroelastomer (A).

13. The method according to claim 1, wherein the cure-site containing monomer of type (CS-N) is selected from the group consisting of:
(CS-N1) perfluorovinyl ethers containing nitrile groups of formula $CF_2$=CF—(OCF$_2$CFX$^{CN}$)$_m$—O—(CF$_2$)$_n$—CN, with $X^{CN}$ being F or CF$_3$, m being 0, 1, 2, 3 or 4; n being an integer from 1 to 12; and
(CS-N2) perfluorovinyl ethers containing nitrile groups of formula $CF_2$=CF—(OCF$_2$CFX$^{CN}$)$_{m'}$—O—CF$_2$—CF(CF$_3$)—CN, with $X^{CN}$ being F or CF$_3$, m' being 0, 1, 2, 3 or 4.

14. The method according to claim 1, wherein the step of molding includes at least one of injection moulding, compression moulding, extrusion moulding, coating, screen printing, forming-in-place, and calendaring the composition (C) into a desired shape.

15. The method according to claim 1, wherein molding is performed under heating at a temperature of at most 195° C., and/or at a temperature of at least 160° C.

16. The method according to claim 1, wherein said heating is pursued for a duration of at least 45 minutes, and/or for a duration of less than 16 hours.

17. The method according to claim 1, wherein molding is performed under heating at a temperature of at most 185° C. and at least 170° C., and wherein heating is pursued for a duration of at least one hour and less than 12 hours.

18. Cured shaped article (P) obtained from the composition (C) using the method according to claim 1, said cured shaped article (P) being selected from the group consisting of sealing articles, including O(square)-rings, packings, gaskets, diaphragms, shaft seals, valve stem seals, piston rings, crankshaft seals, cam shaft seals, oil seals, piping and tubings, flexible hoses, and conduits for delivery of hydrocarbon fluids and fuels.

19. A method for detecting wear/failures in a cured shape article (P) of claim 18, said method comprising monitoring release of bromine-containing compounds from the cured shape article (P).

* * * * *